(12) United States Patent
Sinha et al.

(10) Patent No.: US 8,486,969 B2
(45) Date of Patent: Jul. 16, 2013

(54) THERAPEUTIC COMPOUNDS

(75) Inventors: Santosh C. Sinha, Ladera Ranch, CA (US); Smita S. Bhat, Irvine, CA (US); Todd M. Heidelbaugh, Fountain Valley, CA (US); Daniel W. Gil, Corona Del Mar, CA (US); Ken Chow, Newport Coast, CA (US); Michael E. Garst, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 83 days.

(21) Appl. No.: 12/673,623

(22) PCT Filed: Aug. 14, 2008

(86) PCT No.: PCT/US2008/073094
§ 371 (c)(1),
(2), (4) Date: Nov. 2, 2010

(87) PCT Pub. No.: WO2009/023752
PCT Pub. Date: Feb. 19, 2009

(65) Prior Publication Data
US 2011/0039864 A1    Feb. 17, 2011

Related U.S. Application Data

(60) Provisional application No. 60/955,960, filed on Aug. 15, 2007.

(51) Int. Cl.
| | |
|---|---|
| *A61K 31/495* | (2006.01) |
| *A61K 31/473* | (2006.01) |
| *C07D 215/38* | (2006.01) |
| *C07D 241/36* | (2006.01) |
| *C07D 471/00* | (2006.01) |

(52) U.S. Cl.
USPC ........... 514/314; 544/336; 544/349; 546/112; 546/171; 514/249; 514/311

(58) Field of Classification Search
USPC ........... 546/152, 171; 544/336, 349; 514/247, 514/249, 299, 314
See application file for complete search history.

(56) References Cited

U.S. PATENT DOCUMENTS

| | | | | |
|---|---|---|---|---|
| 6,093,727 | A * | 7/2000 | Wong et al. ............ | 514/299 |
| 6,294,566 | B1 * | 9/2001 | Wong et al. ............ | 514/401 |
| 6,777,426 | B2 * | 8/2004 | Wong et al. ............ | 514/310 |
| 7,141,597 | B2 | 11/2006 | Chow | |

OTHER PUBLICATIONS

Wong et al (1998): STN International HCAPLUS database, (Columbus, Ohio), Accession number: 1998:706207.*
Richard B. Silverman Prodrugs and Drug Delivery Systems, Organic Chemistry of Drug Design and Drug Action, 2d Ed., Elsevier Academic Press: Amsterdam, 2004, pp. 496-557.
Terri L. Messier, High Throughput Assays of Cloned Adrenergic, Muscarinic, Neurokinin, and Neurotrophin Receptors in Living Mammalian Cells, Pharmacology and Toxicology 1995, pp. 308-311.

* cited by examiner

*Primary Examiner* — Golam M M Shameem
(74) *Attorney, Agent, or Firm* — Allergan, Inc.

(57) ABSTRACT

Disclosed herein is compound having a structure

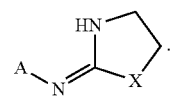

Therapeutic methods, compositions, and medicaments are also disclosed herein.

11 Claims, No Drawings

THERAPEUTIC COMPOUNDS

CROSS REFERENCE TO RELATED APPLICATIONS

This is a national stage application under 35 U.S.C. 371 of PCT patent application PCT/US2008/073094, filed on Aug. 14, 2008, which claims the benefit of U.S. Provisional Patent Application 60/955,960, filed Aug. 15, 2007, each of which is hereby incorporated by reference in its entirety.

BACKGROUND OF THE INVENTION

There is a continuing need for alpha adrenergic compounds for treating pain, glaucoma and other conditions.

DESCRIPTION OF THE INVENTION

Disclosed herein is compound having a structure

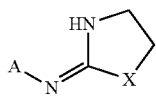

wherein X is O, S, or NH; and
A is a fused bicyclic ring system comprising:
a $C_{3-5}$ alkyl ring moiety fused to a six-membered heteroaromatic ring having 1 or 2 heteroatoms in the ring independently selected from N, O, or S;
wherein the alkyl ring moiety forms the bond depicted as A-N in the structure, said alkyl ring moiety having 0 or 1 $C_{1-4}$ alkyl substituent; and
the heteroaromatic ring has from 0 to 3 substituents independently consisting of: from 0 to 4 carbon atoms, from 0 to 10 hydrogen atoms, from 0 to 2 oxygen atoms, from 0 to 1 sulfur atoms, from 0 to 1 nitrogen atoms, from 0 to 3 fluorine atoms, from 0 to 1 chlorine atoms, and from 0 to 1 bromine atoms.

These compounds are useful for the treatment of pain, glaucoma, and the reduction of intraocular pressure. The compound is incorporated into a dosage form or a medicament and administered to the mammal in need thereof. For example, a liquid composition may be administered as an eye drop for the treatment of glaucoma or lowering intraocular pressure. A solid dosage form may also be administered orally for any of these conditions. Other types of dosage forms and medicaments are well known in the art, and may also be used here.

For the purposes of this disclosure, "treat," "treating," or "treatment" refer to the use of a compound, composition, therapeutically active agent, or drug in the diagnosis, cure, mitigation, treatment, or prevention of disease or other undesirable condition.

Unless otherwise indicated, reference to a compound should be construed broadly to include pharmaceutically acceptable salts, prodrugs, tautomers, alternate solid forms, and non-covalent complexes of a chemical entity of the depicted structure or chemical name.

A pharmaceutically acceptable salt is any salt of the parent compound that is suitable for administration to an animal or human. A pharmaceutically acceptable salt also refers to any salt which may form in vivo as a result of administration of an acid, another salt, or a prodrug which is converted into an acid or salt. A salt comprises one or more ionic forms of the compound, such as a conjugate acid or base, associated with one or more corresponding counter-ions. Salts can form from or incorporate one or more deprotonated acidic groups (e.g. carboxylic acids), one or more protonated basic groups (e.g. amines), or both (e.g. zwitterions).

A prodrug is a compound which is converted to a therapeutically active compound after administration. While not intending to limit the scope of the invention, conversion may occur by hydrolysis of an ester group or some other biologically labile group. Prodrug preparation is well known in the art. For example, "Prodrugs and Drug Delivery Systems," which is a chapter in Richard B. Silverman, *Organic Chemistry of Drug Design and Drug Action*, 2d Ed., Elsevier Academic Press: Amsterdam, 2004, pp. 496-557, provides further detail on the subject.

Tautomers are isomers that are in rapid equilibrium with one another. For example, tautomers may be related by transfer of a proton, hydrogen atom, or hydride ion. Examples of tautomers are depicted below.

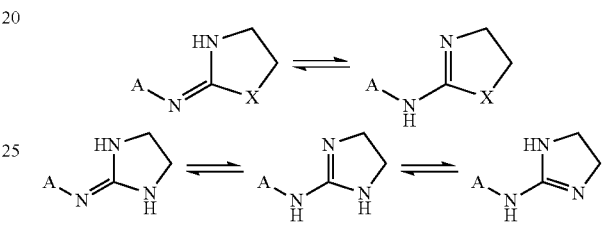

Unless stereochemistry is explicitly depicted, a structure is intended to include every possible stereoisomer, both pure or in any possible mixture.

Alternate solid forms are different solid forms than those that may result from practicing the procedures described herein. For example, alternate solid forms may be polymorphs, different kinds of amorphous solid forms, glasses, and the like.

Non-covalent complexes are complexes that may form between the compound and one or more additional chemical species that do not involve a covalent bonding interaction between the compound and the additional chemical species. They may or may not have a specific ratio between the compound and the additional chemical species. Examples might include solvates, hydrates, charge transfer complexes, and the like.

X is O, S, or NH. Thus, compounds according to any of the structural formulas below are contemplated.

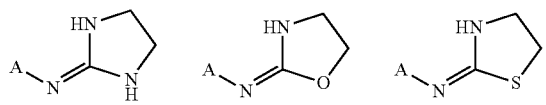

A is a $C_{3-5}$ alkyl ring moiety fused to a six-membered heteroaromatic ring having 1 or 2 heteroatoms in the ring independently selected from N, O, or S. Thus, the core ring structure of A is depicted below.

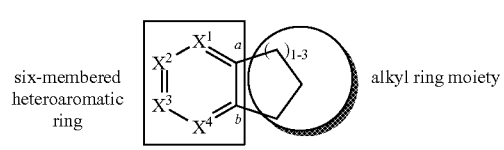

The alkyl ring moiety is depicted in the circle on the right. It is the portion of the ring system that would form a cycloalkyl ring if the two atoms that complete the ring, i.e. the carbons atoms labeled "a" and "b," were both —$CH_2$—. An unsubstituted alkyl ring moiety consists of —$(CH_2)_n$—, wherein n is from 3 to 5. The six-membered heteoaromatic ring is depicted in the rectangle to the left, wherein 1 or 2 of $X^1$, $X^2$, $X^3$, and $X^4$ are independently S, N, or O, and the rest are CH or C—Y, where Y is a substituent as described herein.

Useful examples of the heteroaromatic ring include substituted or unsubstituted pyridine, pyrazine, pyrimidine, and the like.

The alkyl ring moiety forms the bond depicted as A-N in the general structure. In other words, the bridging nitrogen attaches directly to one of the non-aromatic carbons of the alkyl ring moiety.

In other words, the structures depicted below are contemplated.

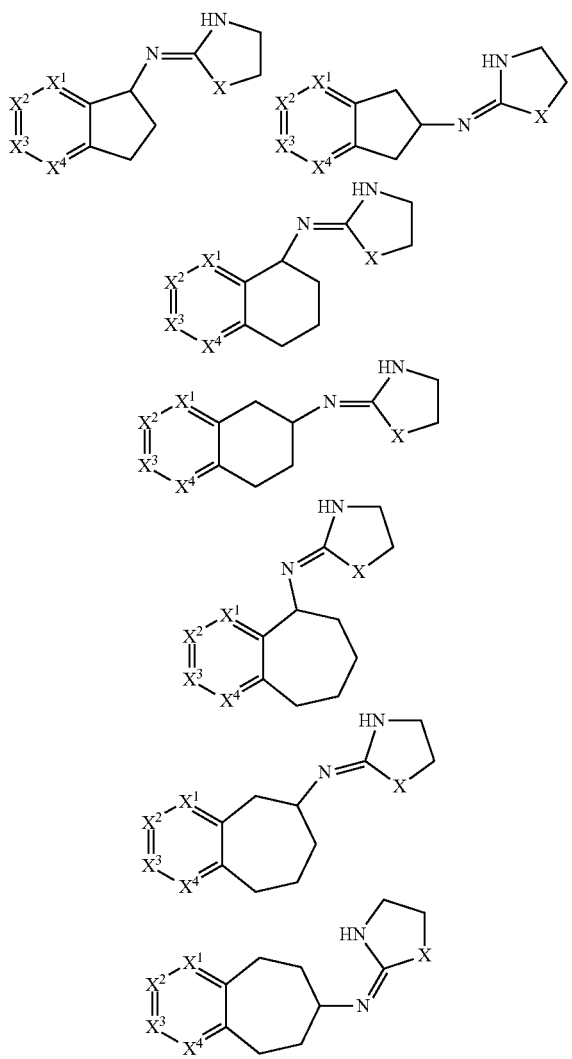

The alkyl ring moiety may be unsubstituted, but it may also have 1 $C_{1-4}$ alkyl substituent.

The substituents on the heteroaromatic ring are stable moieties independently consisting of: from 0 to 4 carbon atoms, from 0 to 10 hydrogen atoms, from 0 to 2 oxygen atoms, from 0 to 1 sulfur atoms, from 0 to 1 nitrogen atoms, from 0 to 3 fluorine atoms, from 0 to 1 chlorine atoms, and from 0 to 1 bromine atoms.

Subject to the constraints described herein (e.g. limits on the number of atoms), examples of these substituents include, but are not limited to:

Hydrocarbyl, meaning a moiety consisting of carbon and hydrogen only, including, but not limited to:
  a. alkyl, meaning hydrocarbyl having no double or triple bonds, including, but not limited to:
     linear alkyl, e.g. methyl, ethyl, n-propyl, n-butyl, etc.,
     branched alkyl, e.g. iso-propyl, t-butyl and other branched butyl isomers, etc.,
     cycloalkyl, e.g. cyclopropyl, cyclobutyl, etc.,
     combinations of linear, branched, and/or cycloalkyl;
  b. alkenyl, e.g. hydrocarbyl having 1 or more double bonds, including linear, branched, or cycloalkenyl
  c. alkynyl, e.g. hydrocarbyl having 1 or more triple bonds, including linear, branched, or cycloalkynyl;
  d. combinations of alkyl, alkenyl, and/or akynyl
  alkyl-CN, such as —$CH_2$—CN, —$(CH_2)_2$—CN; —$(CH_2)_3$—CN, and the like;
  hydroxyalkyl, i.e. alkyl-OH, such as hydroxymethyl, hydroxyethyl, and the like;
  ether substituents, including —O-alkyl, alkyl-O-alkyl, and the like;
  thioether substituents, including —S-alkyl, alkyl-5-alkyl, and the like;
  amine substituents, including —$NH_2$, —NH-alkyl, —N-$alkyl^1 alkyl^2$ (i.e., alkyl and alkyl are the same or different, and both are attached to N), alkyl-$NH_2$, alkyl-NH-alkyl, alkyl-N-$alkyl^1 alkyl^2$, and the like;
  aminoalkyl, meaning alkyl-amine, such as aminomethyl (—$CH_2$-amine), aminoethyl, and the like;
  ester substituents, including —$CO_2$-alkyl, —$CO_2$—phenyl, etc.;
  other carbonyl substituents, including aldehydes; ketones, such as acyl (i.e. $\overset{O}{\underset{\xi}{\overset{\|}{C}}}$ hydrocarbyl), and the like; in particular, acetyl, propionyl, and benzoyl substituents are contemplated;
  fluorocarbons or hydrofluorocarbons such as —$CF_3$, —$CH_2CF_3$, etc.; and
  —CN;
  combinations of the above are also possible, subject to the constraints defined;
  Alternatively, a substituent may be —F, —Cl, —Br, or —I.
  In particular, alkyl having from 1 to 4 carbon atoms is contemplated;

The substituents on the heteroaromatic ring are stable, i.e. they must be stable enough to be stored in a bottle at room temperature under a normal atmosphere for at least 12 hours, or stable enough to be useful for any purpose disclosed herein.

If a substituent is a salt, for example of a carboxylic acid or an amine, the counter-ion of said salt, i.e. the ion that is not covalently bonded to the remainder of the molecule is not counted for the purposes of the number of atoms in the moiety. Thus, for example, the salt —$CO_2^-Na^+$ consists of 1 carbon and 2 oxygen atoms, i.e. sodium is not counted. In another example, the salt —NH(Me)$_2$$^+$Cl$^-$ consists of 2 carbon atoms, 1 nitrogen atom, and 7 hydrogen atoms, i.e. chlorine is not counted.

In another embodiment, the substituents are independently —H, alkyl having from 1 to 4 carbon atoms, —F, —Cl, —Br, —CH$_2$OH, an amine having from 0 to 4 carbon atoms, —CH$_2$CN, —CF$_3$, or acyl having from 1 to 4 carbon atoms.

In another embodiment, the substituents are independently —H, —F, —Cl, —Br, —CH$_3$, —NHCH$_3$, or —CF$_3$.

The substituent of the alkyl ring moiety is H or C$_{1-4}$ alkyl, i.e. methyl, ethyl, n-propyl, iso-propyl, and the butyl isomers. Thus, compounds having any of the structures depicted below are contemplated, wherein the substituent of the alkyl ring is depicted as R$^e$.

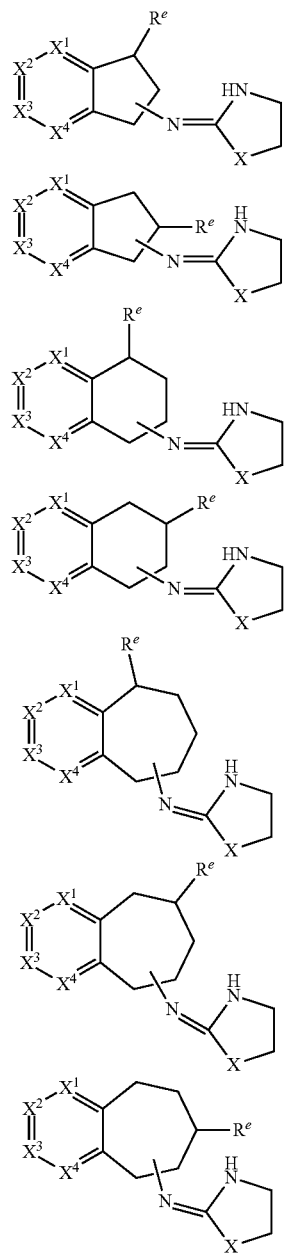

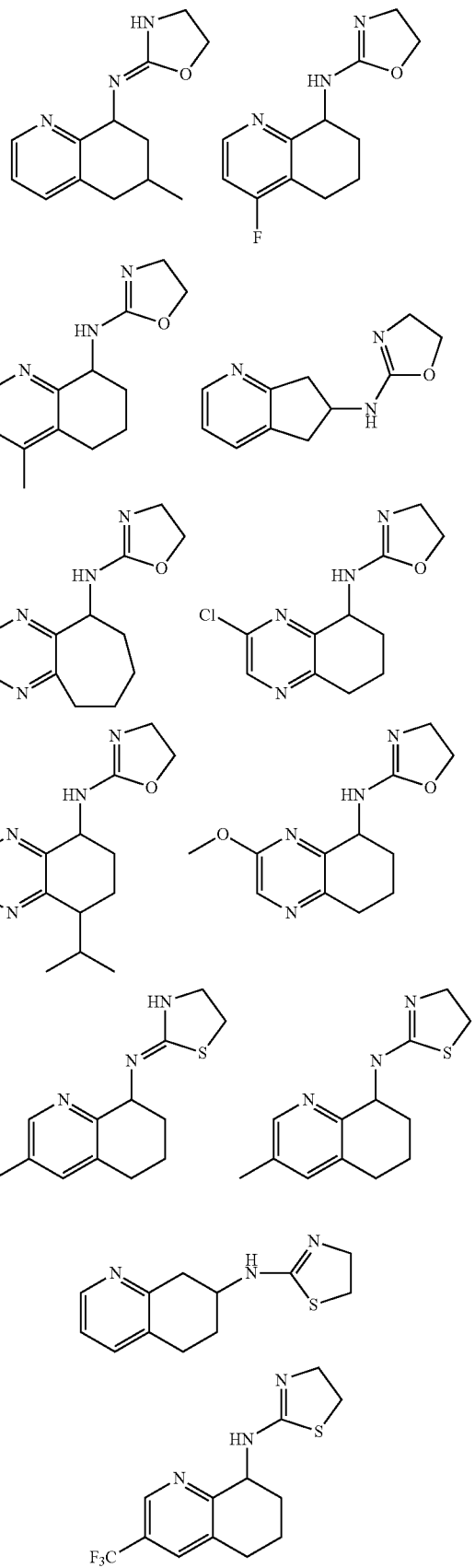

Some hypothetical examples of useful compounds are shown below.

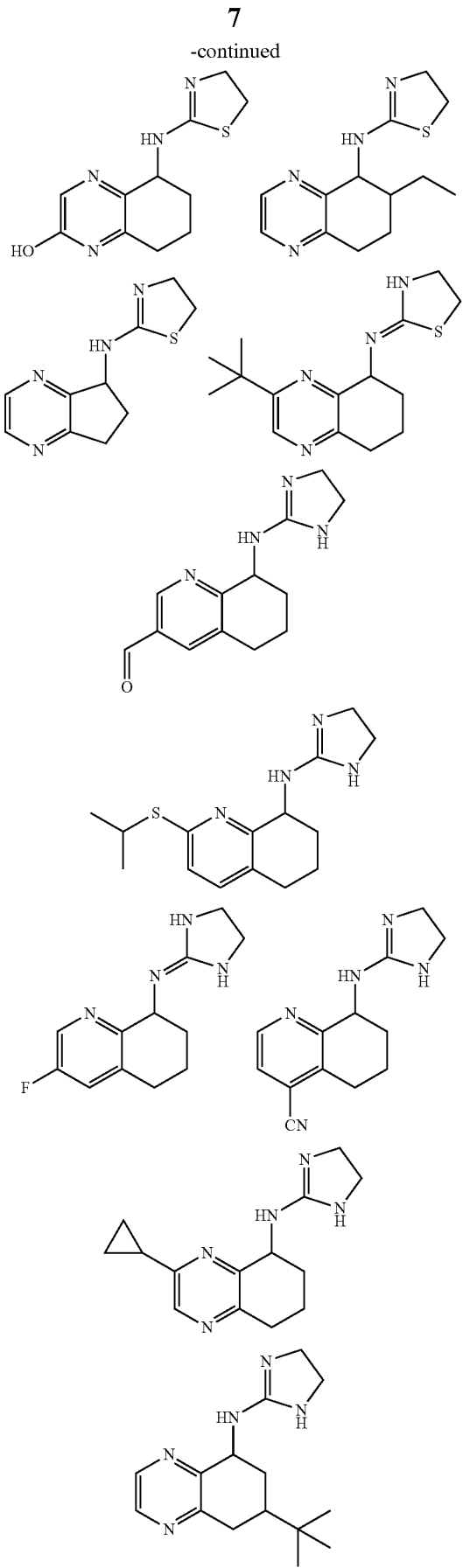
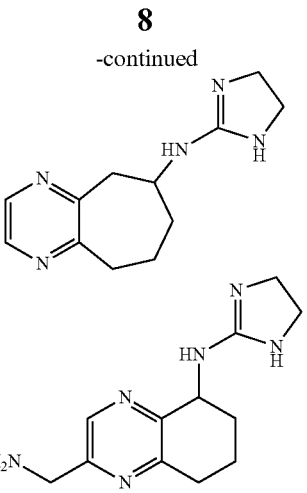

Synthetic Methods

Procedure for the Preparation of (4,5-Dihydro-oxazol-2-yl)-(5,6,7,8-tetrahydro-quinoxalin-5-yl)-amine, 772

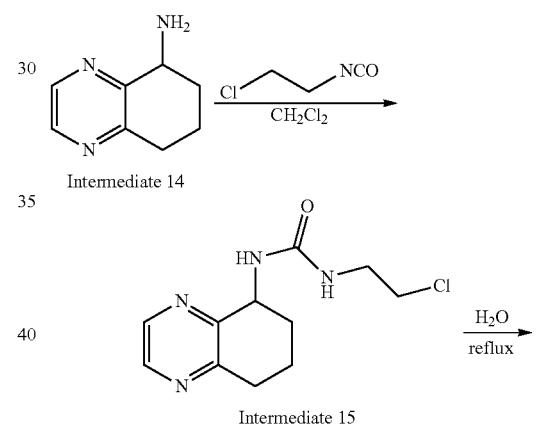

Intermediate 15

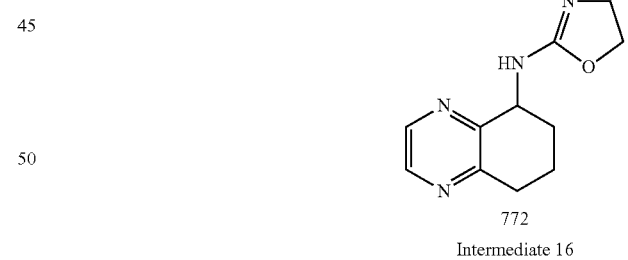

772
Intermediate 16

To 5,6,7,8-tetrahydroquinoxalin-5-amine (Intermediate 14) (3.0 mmol) in dichloromethane (10 mL) was added chloroethylisocyanate (3.3 mmol). The solution was stirred at room temperature for 1.5 hour. The solvents was removed under vacuum. gave a crude material, Intermediate 15.

Intermediate 15 was refluxed in H₂O (60 mL) for 1 hour. After cooling to room temperature, the reaction was basified with NaOH (pH 14), extracted in Ethyl acetate (3×50 mL). The pooled organic layers were washed with brine and dried over magnesium sulphate to give 772.

$^1$HNMR (CDCl$_3$, 300 MHz): δ=8.42 (d, J=6 Hz, 1H), 7.42 (d, J=6 Hz, 1H), 7.13 (dd, J=6, 9 Hz, 1H), 4.88-4.69 (m, 3H), 3.99-3.85 (m, 2H), 2.95-2.87 (m, 1H), 2.80-2.71 (m, 1H), 2.30-2.23 (m, 1H), 2.08-2.01 (m, 2H), 1.89-1.77 (m, 1H).

Procedure for the Preparation of (4,5-Dihydro-oxazol-2-yl)-(5,6,7,8-tetrahydro-quinolin-8-yl)-amine, 747

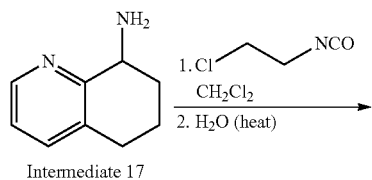

Intermediate 17

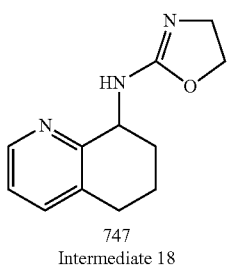

747
Intermediate 18

To 5,6,7,8-tetrahydroquinolin-8-amine (Intermediate 17) (3.0 mmol) in dichloromethane (10 mL) was added chloroethylisocyanate (3.3 mmol). The solution was stirred at room temperature for 1.5 hour. The solvent was removed under vacuum gave a crude material, which was refluxed in H₂O (60 mL) for 1 hour. After cooling to room temperature, the reaction was basified with NaOH (pH 14), extracted in Ethyl acetate (3×50 mL). The pooled organic layers were washed with brine and dried over magnesium sulphate to give 747. (4,5-Dihydro-oxazol-2-yl)-(5,6,7,8-tetrahydro-quinolin-8-yl)-amine, 747 as a solid.

¹HNMR (CDCl₃, 300 MHz): δ=6.89-7.34 (m, 4H), 5.21 (s, J=4.5 Hz, 1H), 4.01-4.07 (m, 2H), 3.34-3.39 (m, 2H), 2.82-2.96 (m, 2H), 2.59-2.67 (m, 1H), 1.91-1.99 (m, 1H).

Synthesis of Amine 14 and 17

Procedure for the Preparation of 5,6,7,8-tetrahydroquinoxalin-5-amine, 14

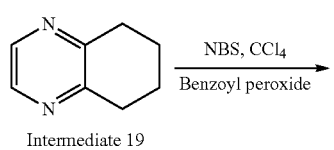

Intermediate 19

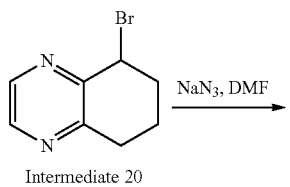

Intermediate 20

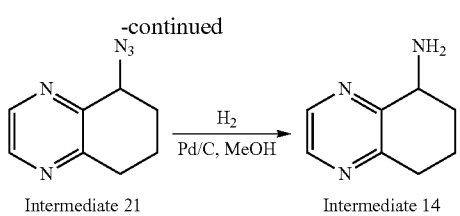

Intermediate 21                    Intermediate 14

To a solution of 5,6,7,8-tetrahydroquinoxaline (Intermediate 19) (3.08 g, 23.0 mmol, commercially available) in CCl₄ (200 mL) was added N-bromosuccinamide (4.09 g, 23.0 mmol) and a catalytic amount (56 mg) of benzoyl peroxide. The reaction mixture was heated at reflux for 17 hours. The reaction mixture was cooled to room temperature and filtered through Celite and concentrated in vacuo gave 5-bromo-5,6,7,8-tetrahydroquinoxaline, (Intermediate 20) (3.8 g, crude).

5-bromo-5,6,7,8-tetrahydroquinoxaline, (Intermediate 20) (3.8 g, 17.92 mmol) and sodium azide (2.3 g, 35.8 mmol) were dissolved in DMF (50 mL) under nitrogen atmosphere and the reaction mixture was warmed to 60° C. for 20 hours. The mixture was cooled to room temperature and poured over water (200 mL), and was extracted with CH₂Cl₂ (3×100 mL). The organic extracts were washed with brine (2 ×100 mL), dried and concentrated in vacuo. The crude material was purified by flash column chromatography on silica gel using 1:1 EtOAc/hexanes to afford 5-azido-5,6,7,8-tetrahydroquinoxaline, (Intermediate 21) (3.2 g, 84%).

A mixture of 5-azido-5,6,7,8-tetrahydroquinoxaline, (Intermediate 21) (3.2 g, 15.09 mmol) in MeOH (40 mL) was treated 10% Pd/C (300 mg) under H₂ atmosphere (balloon) for 16 h at rt. The mixture was filtered through Celite and freed of solvent under reduced pressure. The residue was purified by chromatography on silica gel with 10% MeOH: CH₂Cl₂ to give, 5,6,7,8-tetrahydroquinoxalin-5-amine, (Intermediate 21) (1.3 g). ¹HNMR (CD₃OD, 500 MHz): δ=8.48 (s, 1H), 8.38 (s, 1H), 4.06 (dd, J=5.5, 9 Hz, 1H), 3.02-2.97, (m, 2H), 2.30-2.24 (m, 1H), 2.15-2.08 (m, 1H), 1.96-1.73 (m, 1H).

Procedure for the Preparation of 5,6,7,8-tetrahydroquinolin-5-amine, 17

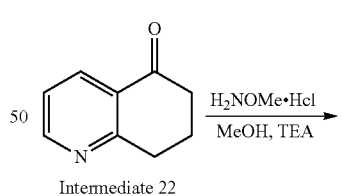

Intermediate 22

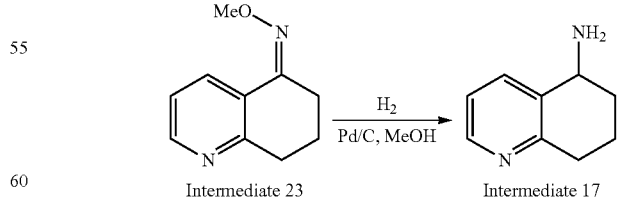

Intermediate 23                    Intermediate 17

To a solution of 7,8-dihydroquinolin-5(6H)-one (Intermediate 22) (1.06 g, 7.2 mmol, commercially available) in MeOH (20 mL) was added methoxylamine (1.2 g, 14.4 mmol) followed by triethyl amine (2 mL, 14.4 mmol). The reaction mixture was heated at reflux for 16 hours. The reaction mixture was cooled to room temperature and concentrated in vacuo. The residue was then diluted in $CH_2Cl_2$ and quenched with water (100 mL), and was extracted with $CH_2Cl_2$ (3×100 mL). The organic extracts were dried and concentrated in vacuo. The crude material was purified by flash column chromatography on silica gel using $MeOH:CH_2Cl_2$ to afford (Z/E)-7,8-dihydroquinolin-5(6H)-one O-methyl oxime, (Intermediate 23) (1.14 g, 90%).

A mixture of Z/E)-7,8-dihydroquinolin-5(6H)-one O-methyl oxime, (Intermediate 23) (1.14 g, 6.47 mmol) in TFA (20 Ml) was added 10% palladium on carbon (10 wt % of Pd/C, 0.15 g) under argon in a Parr shaker flask. The mixture was hydrogenated at 50 psi for 16 hours. The reaction mixture was flushed with nitrogen and filtered through a plug of Celite® and concentrated in vacuo. The crude material was purified by flash column chromatography on silica gel using $NH_3$-$MeOH:CH_2Cl_2$ to afford, 5,6,7,8-tetrahydroquinolin-5-amine, (Intermediate 22), (0.74 g, 78%).

$^1$HNMR ($CD_3OD$, 300 MHz): δ=8.41 (d, J=4.5 Hz, 1H), 7.43 (d, J=8.1 Hz, 1H), 7.15-7.11 (m, 1H), 4.18 (m, 1H), 2.85-2.80, (m, 2H), 2.35-2.29 (m, 1H), 2.05-2.01 (m, 1H), 1.99-1.77 (m, 2H).

Biological Data

Receptor Selection and Amplification Technology (RSAT) Assay

The RSAT assay measures a receptor-mediated loss of contact inhibition that results in selective proliferation of receptor-containing cells in a mixed population of confluent cells. The increase in cell number is assessed with an appropriate transfected marker gene such as β-galactosidase, the activity of which can be easily measured in a 96-well format. Receptors that activate the G protein, Gq, elicit this response. Alpha2 receptors, which normally couple to Gi, activate the RSAT response when coexpressed with a hybrid Gq protein that has a Gi receptor recognition domain, called Gq/i5.

NIH-3T3 cells are plated at a density of 2×106 cells in 15 cm dishes and maintained in Dulbecco's modified Eagle's medium supplemented with 10% calf serum. One day later, cells are cotransfected by calcium phosphate precipitation with mammalian expression plasmids encoding p-SV-β-galactosidase (5-10 μg), receptor (1-2 μg) and G protein (1-2 μg). 40 μg salmon sperm DNA may also be included in the transfection mixture. Fresh media is added on the following day and 1-2 days later, cells are harvested and frozen in 50 assay aliquots. Cells are thawed and 100 μl added to 100 μl aliquots of various concentrations of drugs in triplicate in 96-well dishes. Incubations continue 72-96 hr at 37° C. After washing with phosphate-buffered saline, β-galactosidase enzyme activity is determined by adding 200 μl of the chromogenic substrate (consisting of 3.5 mM o-nitrophenyl-β-D-galactopyranoside and 0.5% nonidet P-40 in phosphate buffered saline), incubating overnight at 30° C. and measuring optical density at 420 nm. The absorbance is a measure of enzyme activity, which depends on cell number and reflects a receptor-mediated cell proliferation. The efficacy or intrinsic activity is calculated as a ratio of the maximal effect of the drug to the maximal effect of a standard full agonist for each receptor subtype. Brimonidine, also called UK14304, the chemical structure of which is shown below, is used as the standard agonist for the $alpha_{2A}$, $alpha_{2B}$ and $alpha_{2C}$ receptors. The $EC_{50}$ is the concentration at which the drug effect is half of its maximal effect.

Brimonidine

The results of the RSAT assay with several exemplary compounds of the invention are disclosed in Table 1 above together with the chemical formulas of these exemplary compounds. $EC_{50}$ values are nanomolar. ND stands for "not determinable" at concentrations less than 10 micromolar. IA stands for "intrinsic activity."

TABLE 1

| Structure | Alpha 2B | Alpha 2C | Alpha 2A |
|---|---|---|---|
| 747 | 545 (67) | nd (22) | nd (3) |
| 772 | 271 (86) | nd (27) | nd (16) |

Methods of formulating these compounds are well known in the art. For example, U.S. Pat. No. 7,141,597 (especially column 10, line 27 to column 14, line 47) contains information that may be used for general guidance. Similar relevant information is also available in numerous other sources. The biological activity of the compounds disclosed herein (e.g. Table 1) may be used for additional general guidance on dosage, depending on the particular use of a compound.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the claims.

What is claimed is:

1. A compound having a structure

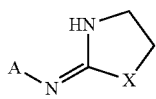

wherein X is O; and
A is a fused bicyclic ring system comprising:
a $C_{3-5}$ alkyl ring moiety fused to a six-membered heteroaromatic ring having 1 or 2 N atoms in the ring;
wherein the alkyl ring moiety forms the bond depicted as A-N in the structure, said alkyl ring moiety having 0 or 1 $C_{1-4}$ alkyl substituent; and
the heteroaromatic ring has from 0 to 3 substituents independently consisting of: from 0 to 4 carbon atoms, from 0 to 10 hydrogen atoms, from 0 to 2 oxygen atoms, from 0 to 1 sulfur atoms, from 0 to 1 nitrogen atoms, from 0 to 3 fluorine atoms, from 0 to 1 chlorine atoms, and from 0 to 1 bromine atoms.

2. The compound of claim 1 having a structure

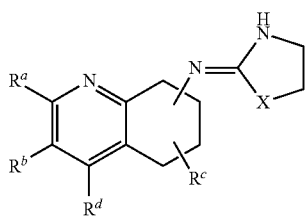

wherein $R^a$, $R^b$, and $R^d$ are independently hydrogen, or stable moieties consisting of from 0 to 4 carbon atoms, from 0 to 10 hydrogen atoms, from 0 to 2 oxygen atoms, from 0 to 1 sulfur atoms, from 0 to 1 nitrogen atoms, from 0 to 3 fluorine atoms, from 0 to 1 chlorine atoms, and from 0 to 1 bromine atoms; and
$R^c$ is hydrogen or $C_{1-4}$ alkyl.

3. The compound of claim 1 having a structure

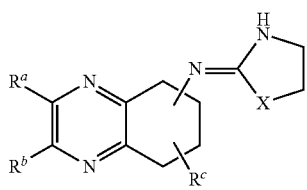

wherein $R^a$ and $R^b$ are independently hydrogen, or stable moieties consisting of from 0 to 4 carbon atoms, from 0 to 10 hydrogen atoms, from 0 to 2 oxygen atoms, from 0 to 1 sulfur atoms, from 0 to 1 nitrogen atoms, from 0 to 3 fluorine atoms, from 0 to 1 chlorine atoms, and from 0 to 1 bromine atoms; and
$R^c$ is hydrogen or $C_{1-4}$ alkyl.

4. The compound of claim 1 wherein the alkyl ring moiety is:

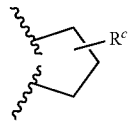

wherein $R^c$ is hydrogen or $C_{1-4}$ alkyl.

5. The compound of claim 1 wherein the alkyl ring moiety is:

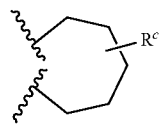

wherein $R^c$ is hydrogen or $C_{1-4}$ alkyl.

6. The compound of claim 2 wherein $R^a$ and $R^b$ are independently methyl, F, Cl, Br, OH, or $CF_3$.

7. The compound of claim 6 wherein $R^c$ is H or methyl.

8. The compound of claim 2 having a structure

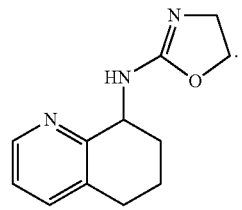 [SMILES: c1cnc2c(c1)CCCC2NC1=NCCO1]

9. The compound of claim 3 having a structure

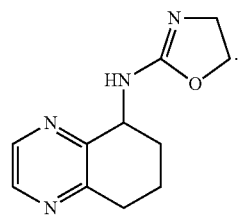 [SMILES: c1cnc2c(n1)CCCC2NC1=NCCO1]

10. A method of reducing intraocular pressure comprising administering a compound according to claim 1 to a mammal in need thereof.

11. A method of treating pain comprising administering a compound according to claim 1 to a mammal in need thereof.

* * * * *

UNITED STATES PATENT AND TRADEMARK OFFICE
CERTIFICATE OF CORRECTION

PATENT NO. : 8,486,969 B2  
APPLICATION NO. : 12/673623  
DATED : July 16, 2013  
INVENTOR(S) : Santosh C. Sinha et al.

Page 1 of 1

It is certified that error appears in the above-identified patent and that said Letters Patent is hereby corrected as shown below:

In the Specification

In column 3, line 6, delete "heteoaromatic" and insert -- heteroaromatic --, therefor.

In column 4, line 27, delete "alkyl-5-alkyl," and insert -- alkyl-S-alkyl, --, therefor.

In column 4, line 30, delete "alkyl and alkyl" and insert -- alkyl$^1$ and alkyl$^2$ --, therefor.

In column 6, lines 42-50, delete " 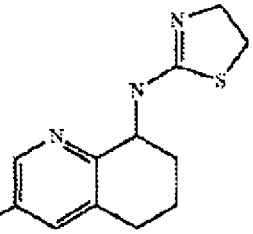 " and insert -- 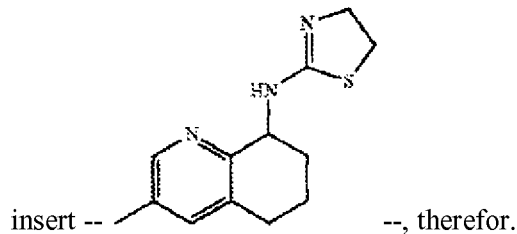 --, therefor.

Signed and Sealed this  
Fifteenth Day of October, 2013

Teresa Stanek Rea  
*Deputy Director of the United States Patent and Trademark Office*